United States Patent
Arba et al.

(10) Patent No.: US 7,147,785 B2
(45) Date of Patent: Dec. 12, 2006

(54) ELECTRODEIONIZATION DEVICE AND METHODS OF USE

(75) Inventors: John W. Arba, Bradford, MA (US); Li-Shiang Liang, Harvard, MA (US); Joseph D. Gifford, Marlborough, MA (US); Devendra Atnoor, Woburn, MA (US); Jonathan H. Wood, Needham, MA (US)

(73) Assignee: USFilter Corporation, Warrendale, PA (US)

( * ) Notice: Subject to any disclaimer, the term of this patent is extended or adjusted under 35 U.S.C. 154(b) by 53 days.

(21) Appl. No.: 10/845,782

(22) Filed: May 13, 2004

(65) Prior Publication Data

US 2005/0016932 A1    Jan. 27, 2005

Related U.S. Application Data

(63) Continuation-in-part of application No. 09/954,986, filed on Sep. 18, 2001, now abandoned.

(60) Provisional application No. 60/236,276, filed on Sep. 28, 2000.

(51) Int. Cl.
    *C02F 1/469*    (2006.01)
(52) U.S. Cl. ...................... 210/748; 210/764; 204/520; 422/28; 422/38
(58) Field of Classification Search ................ 210/644, 210/663, 681, 748, 764, 900, 243; 204/630, 204/518, 520; 422/28, 38
    See application file for complete search history.

(56) References Cited

U.S. PATENT DOCUMENTS

| 2,514,415 A | 7/1950 | Rasch |
| 2,681,319 A | 6/1954 | Bodamer |
| 2,681,320 A | 6/1954 | Bodamer |
| 2,788,319 A | 4/1957 | Pearson |
| 2,794,777 A | 6/1957 | Pearson |
| 2,815,320 A | 12/1957 | Kollsman |
| 2,854,394 A | 9/1958 | Kollsman |
| 2,923,674 A | 2/1960 | Kressman |

(Continued)

FOREIGN PATENT DOCUMENTS

AU    B-18629/92    10/1992

(Continued)

OTHER PUBLICATIONS

Yoram Oren et al., "Studies on polarity reversal with continuous deionization," *Desalination*, Elsevier Scientific Publishing Co., Amsterdam, NL, vol. 86, No. 2, Jun. 1, 1992, pp. 155-171.

(Continued)

*Primary Examiner*—Frank M. Lawrence

(57) ABSTRACT

The present invention generally relates to purification systems, and to sanitization and/or sealing of the purification system. The purification system includes an electrodeionization device which can comprise one or a plurality of stages. The electrodeionization device can be constructed with a resilient sealing member forming a water-tight seal between rigid thermally and dimensionally stable compartment spacers. The construction of the electrodeionization device may allow cycling of hot water and/or other liquids, which, in some cases, can improve efficiency and performance of the electrodeionization device. Moreover, the cycling of hot water and/or other liquids may be used to sanitize the electrodeionization device to at least a pharmaceutically acceptable condition and, preferably, in certain instances, to meet at least minimum requirements according to U.S. Pharmacopoeia guidelines by inactivating any microorganisms present within the electrodeionization device.

16 Claims, 7 Drawing Sheets

U.S. PATENT DOCUMENTS

| | | |
|---|---|---|
| 2,943,989 A | 7/1960 | Kollsman |
| 3,014,855 A | 12/1961 | Kressman |
| 3,074,864 A | 1/1963 | Gaysowski |
| 3,099,615 A | 7/1963 | Kollsman |
| 3,148,687 A | 9/1964 | Dosch |
| 3,149,061 A | 9/1964 | Parsi |
| 3,149,062 A | 9/1964 | Gottschal et al. |
| 3,165,460 A | 1/1965 | Zang et al. |
| 3,291,713 A | 12/1966 | Parsi |
| 3,330,750 A | 7/1967 | McRae et al. |
| 3,341,441 A | 9/1967 | Giuffrida et al. |
| 3,375,208 A | 3/1968 | Duddy |
| 3,627,703 A | 12/1971 | Kojima et al. |
| 3,630,378 A | 12/1971 | Bauman |
| 3,645,884 A | 2/1972 | Gilliland |
| 3,686,089 A | 8/1972 | Korngold |
| 3,755,135 A | 8/1973 | Johnson |
| 3,869,375 A | 3/1975 | Ono et al. |
| 3,869,376 A | 3/1975 | Tejeda |
| 3,870,033 A | 3/1975 | Faylor et al. |
| 3,876,565 A | 4/1975 | Takashima et al. |
| 3,989,615 A | 11/1976 | Kiga et al. |
| 4,032,452 A | 6/1977 | Davis |
| 4,033,850 A | 7/1977 | Kedem et al. |
| 4,089,758 A | 5/1978 | McAloon |
| 4,116,889 A | 9/1978 | Chlanda et al. |
| 4,119,581 A | 10/1978 | Rembaum et al. |
| 4,130,473 A | 12/1978 | Eddleman |
| 4,153,761 A | 5/1979 | Marsh |
| 4,167,551 A | 9/1979 | Tamura et al. |
| 4,191,811 A | 3/1980 | Hodgdon |
| 4,197,206 A | 4/1980 | Karn |
| 4,216,073 A | 8/1980 | Goldstein |
| 4,217,200 A | 8/1980 | Kedem et al. |
| 4,226,688 A | 10/1980 | Kedem et al. |
| 4,228,000 A | 10/1980 | Hoeschler |
| 4,294,933 A | 10/1981 | Kihara et al. |
| 4,298,442 A | 11/1981 | Giuffrida |
| 4,321,145 A | 3/1982 | Carlson |
| 4,330,654 A | 5/1982 | Ezzell et al. |
| 4,358,545 A | 11/1982 | Ezzell et al. |
| 4,374,232 A | 2/1983 | Davis |
| 4,430,226 A | 2/1984 | Hedge et al. |
| 4,465,573 A | 8/1984 | O'Hare |
| 4,473,450 A | 9/1984 | Nayak et al. |
| 4,505,797 A | 3/1985 | Hodgdon et al. |
| 4,574,049 A | 3/1986 | Pittner |
| 4,614,576 A | 9/1986 | Goldstein |
| 4,632,745 A | 12/1986 | Giuffrida et al. |
| 4,636,296 A | 1/1987 | Kunz |
| 4,655,909 A | 4/1987 | Furuno et al. |
| 4,661,411 A | 4/1987 | Martin et al. |
| 4,671,863 A | 6/1987 | Tejeda |
| 4,687,561 A | 8/1987 | Kunz |
| 4,702,810 A | 10/1987 | Kunz |
| 4,707,240 A | 11/1987 | Parsi et al. |
| 4,747,929 A | 5/1988 | Siu et al. |
| 4,747,955 A | 5/1988 | Kunin |
| 4,751,153 A | 6/1988 | Roth |
| 4,753,681 A | 6/1988 | Giuffrida et al. |
| 4,770,793 A | 9/1988 | Treffry-Goatley et al. |
| 4,804,451 A | 2/1989 | Palmer |
| 4,849,102 A | 7/1989 | Latour et al. |
| 4,871,431 A | 10/1989 | Parsi |
| 4,872,958 A | 10/1989 | Suzuki et al. |
| 4,915,803 A | 4/1990 | Morris |
| 4,925,541 A | 5/1990 | Giuffrida et al. |
| 4,931,160 A | 6/1990 | Giuffrida |
| 4,956,071 A | 9/1990 | Giuffrida et al. |
| 4,964,970 A | 10/1990 | O'Hare |
| 4,969,983 A | 11/1990 | Parsi |
| 4,983,267 A | 1/1991 | Moeglich et al. |
| 5,026,465 A | 6/1991 | Katz et al. |
| 5,030,672 A | 7/1991 | Hann et al. |
| 5,066,375 A | 11/1991 | Parsi et al. |
| 5,066,402 A | 11/1991 | Anselme et al. |
| 5,073,268 A | 12/1991 | Saito et al. |
| 5,082,472 A | 1/1992 | Mallouk et al. |
| 5,084,148 A | 1/1992 | Kazcur et al. |
| 5,092,970 A | 3/1992 | Kaczur et al. |
| 5,106,465 A | 4/1992 | Kaczur et al. |
| 5,116,509 A | 5/1992 | White |
| 5,120,416 A | 6/1992 | Parsi et al. |
| 5,126,026 A | 6/1992 | Chlanda |
| 5,128,043 A | 7/1992 | Wildermuth |
| 5,154,809 A | 10/1992 | Oren et al. |
| 5,166,220 A | 11/1992 | McMahon |
| 5,176,828 A | 1/1993 | Proulx |
| 5,196,115 A | 3/1993 | Andelman |
| 5,203,976 A | 4/1993 | Parsi et al. |
| 5,211,823 A | 5/1993 | Giuffrida et al. |
| 5,223,103 A | 6/1993 | Kazcur et al. |
| 5,240,579 A | 8/1993 | Kedem |
| 5,254,227 A | 10/1993 | Cawlfield et al. |
| 5,259,936 A | 11/1993 | Ganzi |
| 5,292,422 A | 3/1994 | Liang et al. |
| 5,308,466 A | 5/1994 | Ganzi et al. |
| 5,308,467 A | 5/1994 | Sugo et al. |
| 5,316,637 A | 5/1994 | Ganzi et al. |
| 5,342,521 A | 8/1994 | Bardot et al. |
| 5,346,624 A | 9/1994 | Libutti et al. |
| 5,346,924 A | 9/1994 | Giuffrida |
| 5,356,849 A | 10/1994 | Matviya et al. |
| 5,358,640 A | 10/1994 | Zeiher et al. |
| 5,376,253 A | 12/1994 | Rychen et al. |
| 5,411,641 A | 5/1995 | Trainham, III et al. |
| 5,425,858 A | 6/1995 | Farmer |
| 5,425,866 A | 6/1995 | Sugo et al. |
| 5,434,020 A | 7/1995 | Cooper |
| 5,444,031 A | 8/1995 | Hayden |
| 5,451,309 A | 9/1995 | Bell |
| 5,458,787 A | 10/1995 | Rosin et al. |
| 5,460,725 A | 10/1995 | Stringfield |
| 5,460,728 A | 10/1995 | Klomp et al. |
| 5,489,370 A | 2/1996 | Lomasney et al. |
| 5,503,729 A | 4/1996 | Batchelder et al. |
| 5,518,626 A | 5/1996 | Birbara et al. |
| 5,518,627 A | 5/1996 | Tomoi et al. |
| 5,536,387 A | 7/1996 | Hill et al. |
| 5,538,611 A | 7/1996 | Otowa |
| 5,538,655 A | 7/1996 | Fauteux et al. |
| 5,539,002 A | 7/1996 | Watanabe |
| 5,547,551 A | 8/1996 | Bahar et al. |
| 5,558,753 A | 9/1996 | Gallagher et al. |
| 5,580,437 A | 12/1996 | Trainham, III et al. |
| 5,584,981 A | 12/1996 | Turner et al. |
| 5,593,563 A | 1/1997 | Denoncourt et al. |
| 5,599,614 A | 2/1997 | Bahar et al. |
| 5,670,053 A | 9/1997 | Collentro et al. |
| 5,679,228 A | 10/1997 | Batchelder et al. |
| 5,679,229 A | 10/1997 | Goldstein et al. |
| 5,714,521 A | 2/1998 | Kedem et al. |
| RE35,741 E | 3/1998 | Oren et al. |
| 5,736,023 A | 4/1998 | Gallagher et al. |
| 5,759,373 A | 6/1998 | Terada et al. |
| 5,762,774 A | 6/1998 | Tessier |
| 5,766,479 A | 6/1998 | Collentro et al. |
| 5,788,826 A | 8/1998 | Nyberg |
| 5,804,055 A | 9/1998 | Coin et al. |
| 5,814,197 A | 9/1998 | Batchelder et al. |
| 5,837,124 A | 11/1998 | Su et al. |
| 5,858,191 A | 1/1999 | DiMascio et al. |
| 5,858,232 A | 1/1999 | Meissner |
| 5,868,915 A | 2/1999 | Ganzi et al. |

| | | | | | | |
|---|---|---|---|---|---|---|
| 5,891,328 | A | 4/1999 | Goldstein | DE | 1 201 055 | | 9/1965 |
| 5,925,240 | A | 7/1999 | Wilkins et al. | DE | 3238280 | A1 | 4/1984 |
| 5,928,807 | A | 7/1999 | Elias | DE | 4016000 | C2 | 11/1991 |
| 5,954,935 | A | 9/1999 | Neumeister et al. | DE | 44 18 812 | A1 | 12/1995 |
| 5,961,805 | A | 10/1999 | Terada et al. | DE | 199 42 347 | A1 | 3/2001 |
| 5,980,716 | A | 11/1999 | Horinouchi et al. | EP | 0170895 | B1 | 2/1986 |
| 6,056,878 | A | 5/2000 | Tessier et al. | EP | 0 503 589 | B1 | 9/1992 |
| 6,099,716 | A | 8/2000 | Molter et al. | EP | 0 621 072 | A2 | 10/1994 |
| 6,103,125 | A | 8/2000 | Kuepper | EP | 0 680 932 | A2 | 11/1995 |
| RE36,972 | E | 11/2000 | Baker et al. | EP | 0803474 | A2 | 10/1997 |
| 6,146,524 | A | 11/2000 | Story | EP | 0 870 533 | A1 | 10/1998 |
| 6,149,788 | A | 11/2000 | Tessier et al. | EP | 1 068 901 | A2 | 1/2001 |
| 6,171,374 | B1 | 1/2001 | Barton et al. | EP | 1 075 868 | A2 | 2/2001 |
| 6,187,154 | B1 | 2/2001 | Yamaguchi et al. | EP | 1 101 790 | A1 | 5/2001 |
| 6,187,162 | B1 | 2/2001 | Mir | EP | 1 106 241 | A1 | 6/2001 |
| 6,190,528 | B1 | 2/2001 | Li et al. | EP | 1172145 | A2 | 1/2002 |
| 6,190,553 | B1 | 2/2001 | Lee | EP | 1222954 | A1 | 7/2002 |
| 6,190,558 | B1 | 2/2001 | Robbins | EP | 1506941 | A1 | 2/2005 |
| 6,193,869 | B1 | 2/2001 | Towe et al. | GB | 776469 | | 6/1957 |
| 6,197,174 | B1 | 3/2001 | Barber et al. | GB | 877239 | | 9/1961 |
| 6,197,189 | B1 | 3/2001 | Schwartz et al. | GB | 880344 | | 10/1961 |
| 6,214,204 | B1 | 4/2001 | Gadkaree et al. | GB | 893051 | A2 | 4/1962 |
| 6,228,240 | B1 | 5/2001 | Terada et al. | GB | 942762 | | 11/1963 |
| 6,235,166 | B1 | 5/2001 | Towe et al. | GB | 1048026 | | 11/1966 |
| 6,248,226 | B1 | 6/2001 | Shinmei et al. | GB | 1137679 | | 12/1968 |
| 6,254,741 | B1 | 7/2001 | Stuart et al. | GB | 1 381 681 | A | 1/1975 |
| 6,258,278 | B1 | 7/2001 | Tonelli et al. | GB | 1448533 | | 9/1976 |
| 6,267,891 | B1 | 7/2001 | Tonelli et al. | JP | 47 49424 | | 12/1972 |
| 6,274,019 | B1 | 8/2001 | Kuwata | JP | 52-71015 | | 6/1977 |
| 6,279,019 | B1 | 8/2001 | Oh et al. | JP | 54-5888 | | 1/1979 |
| 6,284,124 | B1 | 9/2001 | DiMascio et al. | JP | 7155750 | | 6/1995 |
| 6,284,399 | B1 | 9/2001 | Oko et al. | JP | 7-265865 | | 10/1995 |
| 6,296,751 | B1 | 10/2001 | Mir | JP | 09253643 | | 9/1997 |
| 6,303,037 | B1 | 10/2001 | Tamura et al. | JP | 2001-79358 | | 3/2001 |
| 6,342,163 | B1 | 1/2002 | DeLong et al. | JP | 2001-79553 | | 3/2001 |
| 6,375,812 | B1 | 4/2002 | Leonida | JP | 2001-104960 | | 4/2001 |
| 6,402,916 | B1 | 6/2002 | Sampson et al. | JP | 2001-113137 | | 4/2001 |
| 6,402,917 | B1 | 6/2002 | Emery et al. | JP | 2001-113279 | | 4/2001 |
| 6,461,512 | B1 | 10/2002 | Hirayama et al. | JP | 2001-113280 | | 4/2001 |
| 6,471,867 | B1 | 10/2002 | Sugaya et al. | JP | 2001-121152 | | 5/2001 |
| 6,482,304 | B1 | 11/2002 | Emery et al. | JP | 2002-126744 | | 5/2002 |
| 6,607,647 | B1 | 8/2003 | Wilkins et al. | JP | 2005007347 | | 1/2005 |
| 6,607,668 | B1 | 8/2003 | Rela | JP | 2005007348 | | 1/2005 |
| 6,627,073 | B1 | 9/2003 | Hirota et al. | RO | 114 874 | B | 8/1999 |
| 6,648,307 | B1 | 11/2003 | Nelson et al. | WO | WO 92/11089 | | 7/1992 |
| 6,649,037 | B1 | 11/2003 | Jha et al. | WO | WO 95/32052 | | 11/1995 |
| 6,766,812 | B1 | 7/2004 | Gadini | WO | WO 95/32791 | | 12/1995 |
| 6,783,666 | B1 | 8/2004 | Takeda et al. | WO | WO 96/22162 | | 7/1996 |
| 6,808,608 | B1 | 10/2004 | Srinivasan et al. | WO | WO 97/25147 | | 7/1997 |
| 6,824,662 | B1 | 11/2004 | Liang et al. | WO | WO 97/46491 | | 12/1997 |
| 2001/0003329 | A1 | 6/2001 | Sugaya et al. | WO | WO 97/46492 | | 12/1997 |
| 2002/0092769 | A1 | 7/2002 | Benny et al. | WO | WO 98/11987 | | 3/1998 |
| 2002/0144954 | A1 | 10/2002 | Arba et al. | WO | WO 98/17590 | | 4/1998 |
| 2003/0080467 | A1 | 5/2003 | Andrews et al. | WO | WO 98/20972 | | 5/1998 |
| 2003/0089609 | A1 | 5/2003 | Liang et al. | WO | WO 98/58727 | A1 | 12/1998 |
| 2003/0098266 | A1 | 5/2003 | Shiue et al. | WO | WO 99/39810 | | 8/1999 |
| 2003/0155243 | A1 | 8/2003 | Sferrazza | WO | WO 00/30749 | | 6/2000 |
| 2003/0201235 | A1 | 10/2003 | Chidambaran et al. | WO | WO 00/64325 | A2 | 11/2000 |
| 2004/0079700 | A1 | 4/2004 | Wood et al. | WO | WO 00/75082 | A1 | 12/2000 |
| 2005/0103622 | A1 | 5/2005 | Jha et al. | WO | WO 01/49397 | A1 | 7/2001 |
| 2005/0103630 | A1 | 5/2005 | Ganzi et al. | WO | WO 02/04357 | A1 | 1/2002 |
| 2005/0103631 | A1 | 5/2005 | Freydina et al. | WO | WO 02/14224 | A1 | 2/2002 |
| 2005/0103644 | A1 | 5/2005 | Wilkins et al. | WO | WO 02/26629 | A2 | 4/2002 |
| 2005/0103717 | A1 | 5/2005 | Jha et al. | WO | WO 03/086590 | A1 | 10/2003 |
| 2005/0103722 | A1 | 5/2005 | Freydina et al. | | | | |
| 2005/0103723 | A1 | 5/2005 | Wilkins et al. | | | | |
| 2005/0103724 | A1 | 5/2005 | Wilkins et al. | | | | |
| 2005/0109703 | A1 | 5/2005 | Newenhizen | | | | |

FOREIGN PATENT DOCUMENTS

| | | | |
|---|---|---|---|
| CA | 2316012 | A1 | 11/2001 |
| CN | 1044411 | A | 8/1990 |

OTHER PUBLICATIONS

ASTM, "Standard Practice for Calculation and Adjustment of the Langelier Saturation Index for Reverse Osmosis," Designation: D3739-94 (Reapproved 1998), pp. 1-4.

ASTM, "Standard Practice for Calculation and Adjustment of the Langelier Saturation Index for Reverse Osmosis," Designation: D3739-94 (Reapproved 1998), pp. 1-4.

Calay, J.-C. et al., "The Use of EDI to Reduce the Ammonia Concentration in Steam Generators Blowdown of PWR Nuclear Power Plants," *Power Plant Chemistry*, vol. 2, No. 8, 2000, pp. 467-470.

Dimascio et al., "Continuous Electrodeionization: Production of High-Purity Water without Regeneration Chemicals," The Electrochemical Society *Interface*, Fall 1998, pp. 26-29.

Dimascio et al., "Electrodiaresis Polishing (An Electrochemical Deionization Process)," date unknown, pp. 164-172.

International Application No. PCT/US01/30053, International Search Report dated Nov. 6, 2002.

Dow Chemical, "Dowex Marathon A Ion Exchange Resin," published Dec. 1999, Product Literature reprinted from www.dow.com.

Dow Chemical, "Dowex Marathon A2 Ion Exchange Resin," published Nov. 1998, Product Literature reprinted from www.dow.com.

Dupont Product Information, "NAFION Perfluorinated Membranes," printed Nov. 1993, 4 pages.

Dupont Product Information, "Nafion perfluorinated polymer products," Sep. 1998, 4 pages.

Dupont Product Information, "Nafion perfluorinated membranes," Bulletin 97-01, Jan. 14, 1999, 8 pages.

Farmer et al., Capacitive Deionization of $NH_4ClO_4$ Solutions with Carbon Aerogel Electrodes, *J. Appl. Electro-Chemistry*, vol. 26, (1996), pp. 1007-1018.

FDA, "Guide to Inspections of High Purity Water Systems," printed from www.fda.gov. on Dec. 28, 2001, date unknown.

Ganzi, G.C. et al., "Electrodeionization: Theory and Practice of Continuous Electrodeionization," *Ultrapure Water*, Jul./Aug. 1997, pp. 64-69.

Gifford et al., "An Innovative Approach To Continuous Electrodeionization Module And System Design For Power Applications," *Official Proceedings of the 61st Annual Meeting IWC 2000*, Oct. 22-26, 2000, Pittsburgh, PA, Paper No. 0052, pp. 479-485.

G.J. Gittens et al., "The Application of Electrodialysis to Demineralisation," A.I.Ch.E.-I.Chem.E. Symposium Series No. 9, 1965 (London: Instn chem. Engrs), pp. 79-83.

Glueckauf, "Electro-Deionisation Through a Packed Bed," *British Chemical Engineering*, Dec. 1959, pp. 646-651.

Hobro et al., "Recycling of Chromium from Metal Finishing Waste Waters Using Electrochemical Ion Exchange (EIX)," 1994, pp. 173-183, publication and date unknown.

International Search Report for International Application Serial No. PCT/US93/08745, published as International Publication No. WO 94/06850, dated Dec. 30, 1993.

International Search Report for International Application Serial No. PCT/US97/17189, published as International Publication No. WO 98/11987, dated Jan. 15, 1998.

International Search Report for International Application Serial No. PCT/US97/17190, published as International Publication No. WO 98/20972, dated Jan. 15, 1998.

International Search Report for International Application Serial No. PCT/US00/01666, published as International Publication No. WO 00/44477, dated Jun. 13, 2000.

Jha, Anil D. et al., "CEDI: Selecting the Appropriate Configuration," reprinted from *Power Engineering*, Aug. 2000 edition.

Johnson et al., "Desalting by Means of Porous Carbon Electrodes," *Electrochemical Technology*, vol. 118, No. 3, Mar. 1971, pp. 510-517.

Kedem et al., "EDS—Sealed Cell Electrodialysis," *Desalination*, vol. 46, 1983, pp. 291-298.

Kedem et al., "Reduction of Polarization by Ion-Conduction Spacers: Theoretical Evaluation of a Model System," *Desalination*, vol. 27, 1978, pp. 143-156.

Korngold, "Electrodialysis Process Using Ion Exchange Resins Between Membranes," *Desalination*, vol. 16, 1975, pp. 225-233.

Matejka, "Continuous Production of High-Purity Water by Electro-Deionisation," *J. Appl. Chem., Biotechnol.*, vol. 21, Apr. 1971, pp. 117-120.

Purolite Technical Bulletin, Hypersol-Macronet™ Sorbent Resins, 1995.

V. Shaposhnik et al., "Demineralization of water by electrodialysis with ion-exchange membranes, grains and nets," *Desalination*, vol. 133, (2001), pp. 211-214.

R. Simons, "Strong Electric Field Effects on Proton Transfer Between Membrane-Bound Amines and Water," *Nature*, vol. 280, Aug. 30, 1979, pp. 824-826.

R. Simons, "Electric Field Effects on Proton Transfer Between Ionizable Groups and Water in Ion Exchange Membranes," *Electrochimica Acta*, vol. 29, No. 2, 1984, pp. 151-158.

R. Simons, "Water Splitting In Ion Exchange Membranes," Pergamon Press Ltd., 1985, pp. 275-282.

R. Simons, "The Origin and Elimination of Water Splitting in Ion Exchange Membranes During Water Demineralisation By Electrodialysis," *Desalination*, vol. 28, Jan. 29, 1979, pp. 41-42.

USFilter, "H-Series Industrial CDI® Systems," product information, 1998, 4 pgs.

Walters et al., "Concentration of Radioactive Aqueous Wastes," *Industrial and Engineering Chemistry*, Jan. 1955, pp. 61-67.

Warshawsky et al., "Thermally Regenerable Polymerable Polymeric Crown Ethers, II Synthesis and Application in Electrodialysis," pp. 579-584, publication and date unknown.

Wood, Jonathan et al., "Hot Water Sanitization of Continuous Electrodeionization Systems," *Pharmaceutical Engineering*, vol. 20, No. 6, Nov./Dec. 2000, pp. 1-15.

International Search Report for International Application Serial No. PCT/US01/30053, published as International Publication No. WO 02/26629 A2, dated Jun. 11, 2002.

PCT Written Opinion for International Application Serial No. PCT/US01/30053, published as International Publication No. WO 02/26629 A2, dated Jul. 18, 2002.

PCT Written Opinion for International Application Serial No. PCT/US01/30053, published as International Publication No. WO 02/26629 A2, dated Oct. 21, 2002.

PCT International Preliminary Examination Report for International Application Serial No. PCT/US01/30053, published as International Publication No. WO 02/26629 A2, dated Dec. 10, 2002.

ELECTRODEIONIZATION DEVICE AND METHODS OF USE

RELATED APPLICATIONS

This application is a continuation-in-part of U.S. patent application Ser. No. 09/954,986, filed Sep. 18, 2001, entitled "Electrodeionization Device and Methods of Use," by John Arba, et al., now abandoned, which application claims the benefit of U.S. Provisional Patent Application Ser. No. 60/236,276, filed Sep. 28, 2000, entitled "Continuous Electrodeionization Module and System Design for Power Applications," by J. Gifford, et al. All of these applications are incorporated herein by reference.

FIELD OF THE INVENTION

The present invention relates to water purification and, more particularly, to water purification using an electrodeionization device, and to sanitization and/or sealing of the electrodeionization device.

DESCRIPTION OF THE RELATED ART

Electrodeionization is a process for removing ionic or ionizable species from liquids using an electrically active medium and an electric field to influence ion transport. The electrically active medium may function to alternately collect and discharge ionizable species that facilitate the transport of ions by ionic or anionic substitution mechanisms. Electrodeionization devices can include media having permanent or temporary charge, and can be operated to cause electrochemical reactions designed to achieve or enhance performance. Electrodeionization devices typically include an electrically active membrane such as a semipermeable or an ion selective membrane.

An electrodeionization device typically includes alternating electrically active semipermeable anion and cation exchange membranes. Spaces between the membranes can be configured to create liquid flow compartments with inlets and outlets. A transversely applied electric field may be imposed by an external power source through electrodes at the boundaries of the membranes and compartments. Upon imposition of the electric field, ions in the liquid to be purified are attracted to their respective counter-electrodes. The adjoining compartments, bounded by ion selective membranes, become ionically enriched as a result of ion transport. Electrodeionization devices have been described by, for example, Giuffrida et al. in U.S. Pat. Nos. 4,632,745, 4,925,541, and 5,211,823; by Ganzi in U.S. Pat. Nos. 5,259,936, and 5,316,637; by Oren et al. in U.S. Pat. No. 5,154,809; and by Towe et al. in U.S. Pat. No. 6,235,166.

SUMMARY OF THE INVENTION

The present invention generally relates to water purification using an electrodeionization device, and to sanitization and/or sealing of the electrodeionization device. The subject matter of the present invention involves, in some cases, interrelated products, alternative solutions to a particular problem, and/or a plurality of different uses of one or more systems and/or articles.

The present invention provides, in one embodiment, a method for inactivating microorganisms in an electrodeionization device. The method comprises the steps of passing water through the electrodeionization device at a pharmaceutically acceptable sanitization temperature, and maintaining the pharmaceutically acceptable sanitization temperature for a predetermined period of time.

In another embodiment, the present invention is directed to a water purification system. The water purification system comprises an electrodeionization device fluidly connected to a heating device, and a controller for regulating a flow and temperature of water at a pharmaceutically acceptable level in the electrodeionization device.

In another embodiment, the present invention provides a method for disinfecting an electrodeionization device. The method comprises the step of passing a disinfecting solution at a temperature sufficient to inactivate any microorganisms in the electrodeionization device.

In another embodiment, the present invention is directed to an electrodeionization device. The electrodeionization device comprises a spacer constructed of a material that is dimensionally stable at a temperature that sanitizes the electrodeionization device for pharmaceutical service.

In another embodiment, the present invention provides a method for purifying water. The method comprises the steps of passing water to be purified through the electrodeionization device, and passing water at a temperature greater than about 65° C. through the electrodeionization device for a predetermined period.

In another embodiment, the present invention is directed to an electrodeionization device. The electrodeionization device comprises a rigid depleting compartment spacer having a groove formed on a side thereon, a rigid concentrating compartment spacer that mates with the depleting compartment, and a resilient member disposed within the groove, forming a water-tight seal between the depleting compartment and the concentrating compartment spacers.

In another embodiment, the present invention provides a method for purifying water. The method comprises the steps of passing water to be purified through an electrodeionization device comprising a depleting compartment spacer having a groove formed on a side thereon, a concentrating compartment spacer, and a resilient member disposed within the groove, forming a water-tight seal between the depleting compartment and the concentrating compartment spacers; and applying an electric field across the electrodeionization device.

In another embodiment, the present invention is directed to an electrodeionization device. The electrodeionization device comprises a depleting compartment spacer, a concentrating compartment spacer, and a water-tight seal positioned between a depleting compartment and the concentrating compartment spacers. The water-tight seal comprises an elastomeric sealing member disposed within a groove formed on a surface of either the depleting compartment or the concentrating compartment spacers.

In another embodiment, the present invention provides a method for purifying water. The method comprises the step of passing water to be purified through an electrodeionization device comprising a depleting compartment spacer, a concentrating compartment spacer, and a water-tight seal comprising an elastomeric sealing member disposed within a groove formed on a surface of either the depleting compartment and or the concentrating compartment spacers.

In another embodiment, the present invention is directed to an electrodeionization device. The electrodeionization device comprises a depleting compartment spacer and a concentrating compartment spacer separated by an ion selective membrane, a primary seal positioned between the depleting compartment and the concentrating compartment spacers and secured to the ion selective membrane, and a secondary seal positioned between the depleting compartment and the concentrating compartment spacers.

In another embodiment, the present invention provides a method for facilitating water purification. The method comprises the step of providing an electrodeionization device comprising a depleting compartment spacer and a concentrating compartment spacer, and a water-tight seal positioned between the depleting compartment and the concentrating compartment spacers.

In another embodiment, the present invention provides a method for facilitating water purification. The method comprises the step of providing an electrodeionization device comprising a depleting compartment spacer having a groove formed on a side thereon, a concentrating compartment spacer, and a resilient member disposed within the groove, forming a water-tight seal between the depleting compartment and the concentrating compartment spacers.

In another embodiment, the present invention provides a method for facilitating water purification. The method comprises the step of providing an electrodeionization device comprising a spacer constructed of a material that is dimensionally stable at a temperature greater than about 65° C.

In another embodiment, the present invention is directed to an electrodeionization device. The electrodeionization device comprises a spacer constructed of a material that is dimensionally stable at a temperature greater than about 65° C.

In another embodiment, the present invention provides a method for facilitating inactivation of microorganisms. The method comprises the steps of providing an electrodeionization device fluidly connectable to a heating device, and providing a controller for regulating a flow and a temperature of water at a pharmaceutically acceptable level in the electrodeionization device.

In another embodiment, the present invention provides a method for inactivating microorganisms. The method comprises the steps of passing water through a depleting compartment at a pharmaceutically acceptable sanitization temperature, and maintaining the pharmaceutically acceptable sanitization temperature for a predetermined period of time.

In another embodiment, the present invention provides a method for inactivating microorganisms. The method comprises the steps of passing water through a concentrating compartment at a pharmaceutically acceptable sanitization temperature, and maintaining the pharmaceutically acceptable sanitization temperature for a predetermined period of time.

In one embodiment, the present invention provides a method for inactivating microorganisms in an electrodeionization device. The method comprises steps of heating a liquid to at least a pharmaceutically acceptable sanitization temperature, and passing the liquid through at least a portion of an electrodeionization device.

In another embodiment, the present invention provides a method for inactivating microorganisms in an electrodeionization device. The method comprises a step of heating a liquid contained within an electrodeionization device at a rate of at least about 5° C./min.

In one embodiment, the present invention is directed to a water purification system. The water purification system comprises an electrodeionization device fluidly connected to a source of a liquid that has a temperature that is about or at least a pharmaceutically acceptable sanitization temperature.

In another embodiment, the present invention is directed to a water purification system. The water purification system comprises an electrodeionization device fluidly connected to a heating device able to heat a liquid introduced to the electrodeionization device.

In another embodiment, the present invention is directed to a water purification system. The water purification system comprises an electrodeionization device comprising a spacer constructed of a material that is dimensionally stable at a temperature that sanitizes the electrodeionization device for pharmaceutical service. The electrodeionization device is in fluid communication with a source of a liquid having a temperature that is about or at least a pharmaceutically acceptable sanitization temperature.

In another embodiment, the present invention is directed to a water purification system. The water purification system comprises an electrodeionization device, comprising a rigid depleting compartment spacer having a groove formed on a side thereon, a rigid concentrating compartment spacer that mates with the depleting compartment spacer, and a resilient member disposed within the groove forming a water-tight seal between the depleting compartment and the concentrating compartment spacers. The electrodeionization device is in fluid communication with a source of a liquid having a temperature that is about or at least a pharmaceutically acceptable sanitization temperature.

In another embodiment, the present invention is directed to a water purification system. The water purification system comprises an electrodeionization device comprising a depleting compartment spacer, a concentrating compartment spacer, and a water-tight seal positioned between the depleting compartment and the concentrating compartment spacers, wherein the water-tight seal comprises an elastomeric sealing member disposed within a groove formed on a surface of either the depleting compartment or the concentrating compartment spacers. The electrodeionization device is in fluid communication with a source of a liquid having a temperature that is about or at least a pharmaceutically acceptable sanitization temperature.

In another embodiment, the present invention is directed to a water purification system. The water purification system comprises an electrodeionization device comprising a depleting compartment spacer and a concentrating compartment spacer separated by an ion selective membrane, a primary seal positioned between the depleting compartment and the concentrating compartment spacers and securing the ion selective membrane, and a secondary seal positioned between the depleting compartment and the concentrating compartment spacers. The electrodeionization device is in fluid communication with a source of a liquid having a temperature that is about or at least a pharmaceutically acceptable sanitization temperature.

In another embodiment, the present invention is directed to a water purification system. The water purification system comprises an electrodeionization device comprising a spacer constructed of a material that is dimensionally stable at a temperature greater than about 65° C. The electrodeionization device is in fluid communication with a source of a liquid having a temperature that is about or at least a pharmaceutically acceptable sanitization temperature.

Other advantages, novel features and objects of the invention will become apparent from the following detailed description of the invention when considered in conjunction with the accompanying drawings, which are schematic and are not intended to be drawn to scale. In the figures, each identical, or substantially similar component that is illustrated in various figures is represented by a single numeral or notation. For purposes of clarity, not every component is labeled in every figure, nor is every component of each embodiment of the invention shown where illustration is not necessary to allow those of ordinary skill in the art to understand the invention.

BRIEF DESCRIPTION OF THE DRAWINGS

Preferred, non-limiting embodiments of the present invention will be described by way of example and with reference to the accompanying drawings, in which.

DETAILED DESCRIPTION

Figure 1:
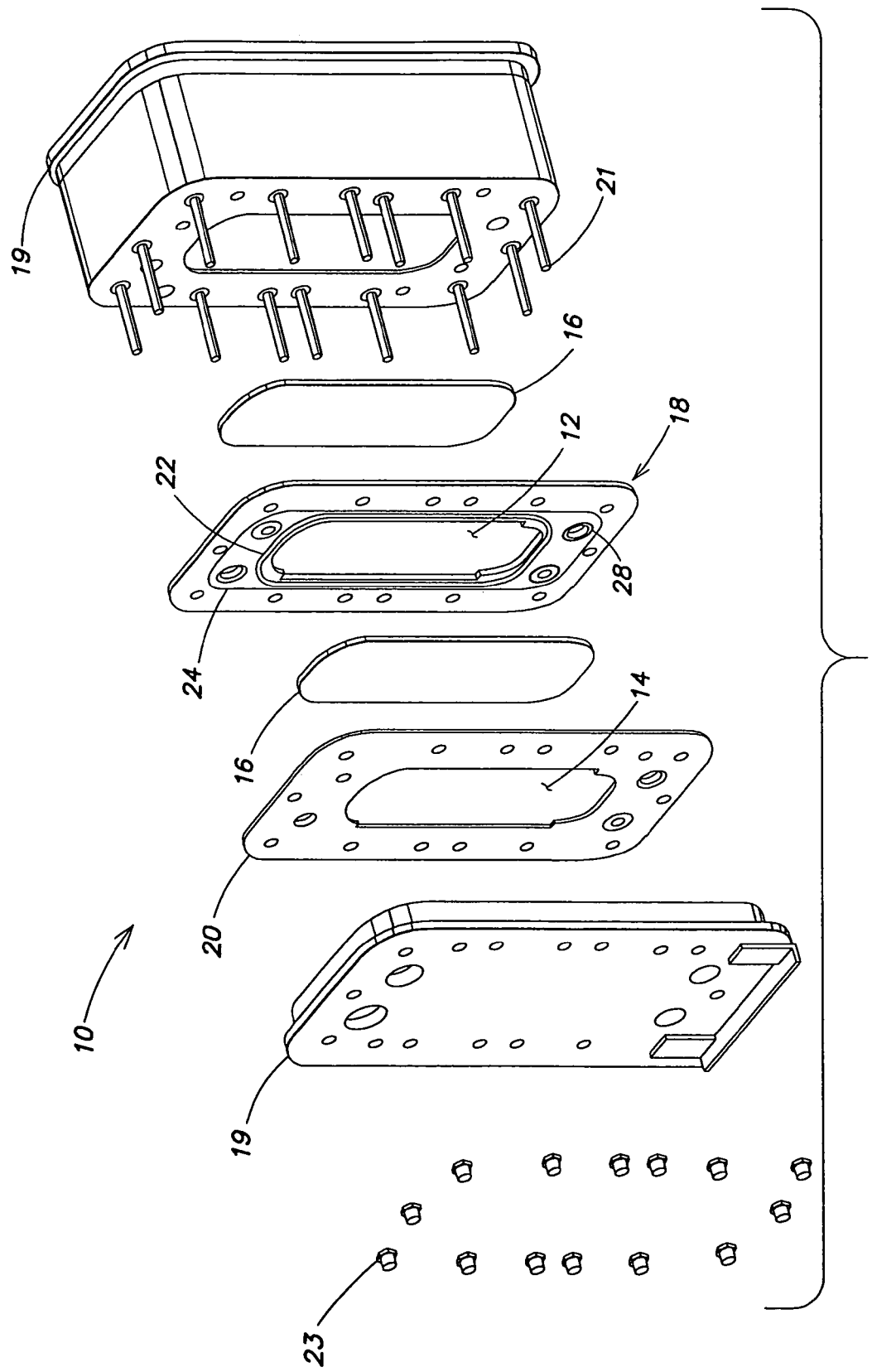
FIG. 1 is an exploded view of an electrodeionization device according to one embodiment of the invention.

The present invention is directed to a water purification system for providing purified water for industrial, commercial, and/or residential applications. The purification system includes an electrodeionization device which can comprise one or a plurality of stages. The electrodeionization device can be constructed with a resilient sealing member forming a water-tight seal between rigid thermally and dimensionally stable compartment spacers. The construction of the electrodeionization device may allow cycling of hot water and/or other liquids, which, in some cases, can improve efficiency and performance of the electrodeionization device. Moreover, the cycling of hot water and/or other liquids may be used to sanitize the electrodeionization device to at least a pharmaceutically acceptable condition and, preferably, in certain instances, to meet at least minimum requirements according to U.S. Pharmacopoeia guidelines by inactivating any microorganisms present within the electrodeionization device. In the device, an anode may be positioned at an opposite end of a stack of depleting and concentrating compartments from within which a cathode is positioned. Each anode and cathode may be provided with an electrode spacer and an ion selective membrane, wherein electrolyte can pass through the electrode spacer.

The liquid, typically comprising water, to be purified can be passed in parallel through each depleting compartment, and a second liquid can be passed through each concentrating compartment in each stage, to effect removal of ions and/or ionic species from the first liquid in depleting compartment to the second liquid in the concentrating compartment. Examples of ions that may be dissolved in the water to be purified include sodium, chloride, potassium, magnesium, calcium, iron, etc. Electrolytes may be passed through the spacer adjacent each electrode in the electrodeionization device. Other possible flow arrangements are possible. For example, counter-curve flow and reverse flow are shown such as those disclosed by, for example, Giuffrida et al. in U.S. Pat. No. 4,632,745, which is incorporated by reference in its entirety. The liquid to be purified can contain other species, for example dissolved or suspended therein, such as ions and ionic species, organics, etc. The liquid to be purified may contain, for example, at least about 20 wt %, at least about 15 wt %, at least about 10 wt %, at least about 5 wt %, at least about 3 wt %, at least about 1 wt %, at least about 0.5 wt %, or at least about 0.1 wt % of one or more species contained therein. In other cases, the water or other liquid to be purified may contain a smaller percentage of species therein. In one embodiment, the liquid to be purified consists essentially of water (i.e., the water may include other ions, salts, suspension matter, etc., so long as those of ordinary skill in the art would consider the liquid to be essentially water, for example, the liquid may be tap water, filtered water, etc).

FIG. 1 shows an exploded view of an electrodeionization device according to one embodiment of the present invention. The electrodeionization device 10 includes a depleting compartment 12 and a concentrating compartment 14. Ion-selective membranes may form the border between the depleting compartment 12 and concentrating compartment 14. Electrodeionization device 10 typically includes a plurality of depleting compartments 12 and concentrating compartments 14, which can be arranged as a stack as shown in FIG. 1. Depleting compartment 12 is typically defined by a depleting compartment spacer 18 and concentrating compartment 14 is typically defined by a concentrating compartment spacer 20. An assembled stack may be bound by end blocks 19 at each end and can be assembled using tie rods 21 secured with nuts 23. In certain embodiments, the compartments include cation-selective membranes and anion-selective membranes, which are typically peripherally sealed to the periphery of both sides of the spacers. The cation-selective membranes and/or anion-selective membranes may be formed from ion exchange powder, a powder binder (e.g., polyethylene) and/or a lubricant (e.g., glycerin). In some embodiments, the cation- and/or anion-selective membranes are heterogeneous polyolefin-based membranes, which are typically extruded by a thermoplastic process using heat and pressure to create a composite sheet.

Depleting compartment 12 and concentrating compartment 14 may be filled with ion exchange resin (not shown). In some embodiments, the depleting and concentrating compartments may be filled with cation exchange and/or anion exchange resin. The cation exchange and/or anion exchange resin may be arranged in a variety of configurations within each of the depleting and concentrating compartments. For example, the cation exchange and/or anion exchange resin can be arranged in layers so that a number of layers in a variety of arrangements can be constructed. Other embodiments or configurations within the scope of the invention include, for example, the use of mixed bed ion exchange resin in any of the depleting, concentrating, and/or electrode compartments; the use of inert resin between layered beds of anion and/or cation exchange resin; or the use of various types of anionic and/or cationic resin including, but not limited to, those described by DiMascio et al., in U.S. Pat. No. 5,858,191, which is incorporated by reference in its entirety.

In operation, a liquid to be purified, typically having dissolved cationic and anionic components, is introduced into the depleting compartment 12. An electric field can be applied across one or more compartments of the electrodeionization device, which may promote migration of ionic species towards their respective attracting electrodes. Under the influence of the electric field, cationic and anionic components may leave the depleting compartments and migrate into the concentrating compartments. Ion selective membranes 16 may block or at least inhibit migration of the cationic and anionic species to the next compartment. The electrodeionization device thus may be used to produce a product that consists essentially of water, and in some cases, is essentially water, i.e., the water may have a trace or undetectable amount of ions, etc., but the water would be considered by those of ordinary skill in the art to be "pure."

In some embodiments, the applied electric field on electrodeionization device 10 creates a polarization phenomenon, which may lead to the dissociation of water into hydrogen and hydroxyl ions. The hydrogen and hydroxyl ions may regenerate the ion exchange resins so that removal of dissolved ionic components from the ion exchange resins can occur continuously and without a step for regenerating ion exchange resins exhausted as a result of ionic species migration. The electric field applied to electrodeionization device 10 is typically direct current. However, any applied current that creates a bias or potential difference between one electrode and another can be used to promote migration of the ionic species within the electrodeionization device.

The ion exchange resin typically utilized in the depleting and/or concentrating compartments can have a variety of functional groups on their surface regions including, but not limited to, tertiary alkyl amino groups and dimethyl ethanolamine. These can also be used in combination with ion exchange resin materials having other functional groups on their surface regions, such as ammonium groups. Other modifications and equivalents useful in ion exchange resin material are within the scope of those persons of ordinary skill in the art, and/or can be ascertained using no more than routine experimentation. Other examples of ion exchange resin include, but are not limited to, DOWEX® MONOSPHERE™ 550A anion resin, MONOSPHERE™ 650C cation resin, MARATHON™ A anion resin, and MARATHON™ C cation resin, all available from the Dow Chemical Company (Midland, Mich.). Non-limiting representative suitable ion selective membranes include homogenous-type web supported styrene-divinyl benzene-based with sulphonic acid or quaternary ammonium functional groups, heterogeneous type web supported using styrene-divinyl benzene-based resins in a polyvinylidene fluoride binder, homogenous type unsupported-sulfonated styrene and quaternized vinyl benzyl amine grafts of polyethylene sheet.

To prevent or at least inhibit leakage of ions and/or liquid from the depleting compartment to the concentrating compartment and vice versa, the ion selective membrane sandwiched between depleting compartment and concentrating compartment spacers may form a substantially water-tight seal. Typically, the spacers and the ion selective membranes are compressed together and fixed in position, for example, with nuts 23 and tie bars 21. In one embodiment of the present invention, as shown in the cross-sectional view of FIG. 2, depleting compartment 12, positioned between concentrating compartments 14, can be defined, at least in part, by the cavity formed between depleting compartment spacer 18 and ion-selective membranes 16. Similarly, concentrating compartment 14 is a cavity that may be defined, at least in part, between concentrating compartment spacer 20 and by selective membranes 16. Also shown in the embodiment of FIG. 2, two water-tight seals 22 and 24 can be used to prevent leakage from and between depleting compartment 12 and concentrating compartment 14. Seals 22 and 24, positioned between the depleting compartment and concentrating compartment spacers, may comprise a resilient sealing member disposed within a groove formed on a surface of the depleting compartment spacer. In another embodiment, the present invention provides a compartment spacer having a groove formed on one side of the spacer. For example, the groove may be disposed around a perimeter of depleting compartment 12 or concentrating compartment 14. Resilient sealing member 26 may be dimensionally constructed and arranged to at least partially fit (and may be compressed in some cases) within the groove formed on the surface of the spacer when the electrodeionization device is assembled.

Figure 2:
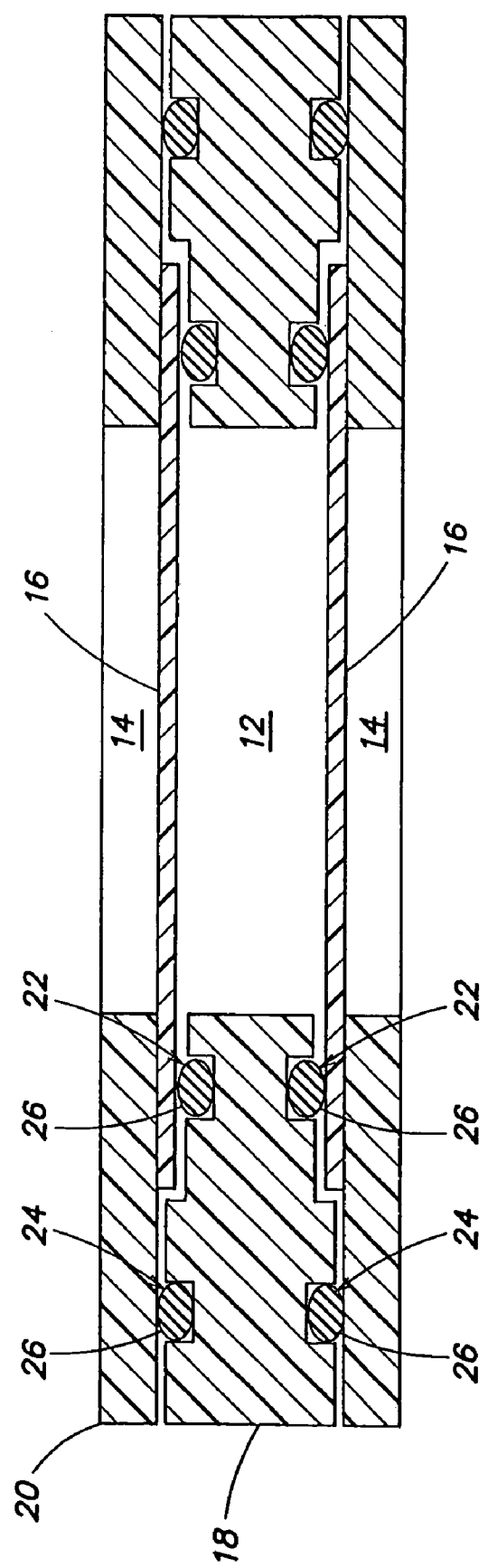
FIG. 2 is a cross-sectional view of an electrodeionization device of the present invention showing a depleting compartment between a concentrating department.

As shown in the embodiment of FIG. 2, grooves are formed on a surface of depleting compartment spacer 18. However, other embodiments are also considered to be within the scope of the present invention. For example, electrodeionization device 10 may include a single seal comprising a groove defined on the surface of the concentrating compartment spacer 20, with a resilient sealing member disposed and compressed therein, thereby forming a water-tight seal between depleting compartment spacer 18 and concentrating compartment spacer 20. The present invention also contemplates, in other embodiments, the use of a plurality of seals, such as primary seal 22 with secondary seal 24.

With reference to FIG. 1, in another embodiment, the invention provides port seals 28 that may form a water-tight seal, around fluid ports, and/or between adjacent spacers. Port seals 28 typically comprise a resilient sealing member, which may be similar to resilient sealing member 26. The port seal, in some cases, may be compressed within a groove surrounding a fluid connection port. Thus, as assembled, the resilient sealing member may prevent or at least inhibit leaks to and from the fluid port.

In another embodiment, the present invention provides the use of thermally stable materials that are suitable for thermal cycling and other thermal changes (i.e., changes in temperature). As defined herein, a "thermally suitable material" is one that can maintain its dimensional stability, having no significant change in dimension or shape or mechanical properties under the influence of temperature and/or pressure. Accordingly, in one embodiment, the present invention contemplates the use of rigid polymeric or non-metallic materials in the construction and assembly of certain electrodeionization devices. Examples of polymeric materials include, but are not limited to, polysulfone, polyphenylsulfone, polyphenylene oxide, polyphenylene ether, chlorinated poly(vinyl chloride), polyphenylene sulfide, polyetherimide, polyetherketone, polyamide-imide and polybenzimidazole, and mixtures thereof. The resilient sealing member may be formed from any material such as an elastomer including, for example, silicon, polyisobutylene, ethylene-propylene, chlorosulfonated polyethylene, polyurethane, or any chlorinated elastomer that is chemically inert and thermally stable to 80° C.

The electrodeionization device, in one set of embodiments, may be disinfected or sanitized by introducing a disinfectant solution or other liquid able to inactivate some or all of the microorganisms present within the electrodeionization device. As used herein, an "inactivated microorganism" is one that is destroyed or killed, or otherwise incapable of propagating into or forming other organisms. While there is no United States Pharmacopoeia specification for bacterial or microorganisms, the recommended action level limit is 100 colony forming units per milliliter for purified water.

Thus, in some embodiments, the present invention provides disinfection of an electrodeionization device by the use of a liquid, for example, hot water or another heated liquid, to inactivate some or all of the microorganisms. The liquid may be heated within the device, and/or externally of the device, using any suitable technique known to those of ordinary skill in the art. Thus, in one embodiment, the liquid is heated externally of the electrodeionization device before being introduced to the device; in another embodiment, the liquid is heated within the electrodeionization device; in another embodiment, the liquid is heated externally of the device, then further heated within the electrodeionization device (for example, to maintain and/or raise the temperature of the liquid within the electrodeionization device, for instance to a pharmaceutically acceptable sanitization temperature).

According to one embodiment, sanitization may be performed by passing and/or circulating a liquid such as hot water through the electrodeionization device, for example, passing and/or circulating a liquid at at least the pharmaceutically acceptable sanitization temperature through the electrodeionization device, for instance, for a predetermined period of time, and/or for at least time necessary to reduce the number of active microorganisms within the electrodeionization device to a pharmaceutically acceptable level. In some cases, the liquid may be passed through a portion of the electrodeionization device, for example, through one or more concentrating compartments and/or one or more depleting compartments.

A "pharmaceutically acceptable sanitization temperature," as used herein, is one where a substantial number of microorganisms exposed to such a temperature are inactivated and, in particular, to one wherein the number of microorganisms is inactivated to below an acceptable action limit or a pharmaceutically acceptable level, for example, to below 1000 colony forming units/ml, below 100 colony forming units/ml, or below 10 colony forming units/ml. In one embodiment, the present invention provides for the passing and/or circulation of hot water or other liquids having a temperature of at least about 65° C. or at least about 80° C. through an electrodeionization device. In another embodiment, the liquid used to disinfect the electrodeionization device may be heated at a rate of at least about 5° C./min, at least about 10° C./min, at least about 15° C./min, or at least about 20° C./min, etc., and the liquid may be heated within and/or externally of the electrodeionization device. The liquid may be heated for any suitable length of time, for example, for a predetermined length of time (e.g., for at least 5 minutes, at least 10 minutes, at least 15 minutes, at least 20 minutes, at least 30 minutes, at least 45 minutes, at least 60 minutes, etc.), and/or for a time necessary to reduce the number of active microorganisms within the device to a pharmaceutically acceptable level.

In some cases, the disinfectant liquid passed through the electrodeionization device comprises water, e.g. as described above. In one embodiment, the disinfectant liquid consists essentially of water (i.e., the liquid may include other ions, salts, suspension matter, etc., so long as those of ordinary skill in the art would consider the liquid to be essentially water, for example, the liquid may be tap water, filtered water, etc). In another embodiment, the disinfectant liquid consists of water, i.e., the water may have a trace or undetectable amount of ions, etc., but the water would be considered "pure" by those of ordinary skill in the art. In still other embodiments, additional materials such as disinfectants, salts, or the like may be added to the disinfectant liquid. For example, the disinfectant liquid may include phenolics, alcohols (e.g., isopropanol, isobutanol, ethanol, etc.), halogens (e.g., dissolved chlorine, bromine, etc.), heavy metals (e.g., silver nitrate, etc.), quaternary ammonium compounds, detergents, aldehydes (e.g., formaldehyde, glutaraldehyde, etc.), gases (e.g., carbon dioxide, ethylene oxide, ozone, etc.), or the like.

The function and advantage of these and other embodiments of the present invention can be further understood from the examples below. The following examples are intended to illustrate the benefits of the present invention but do not exemplify the full scope of the invention.

EXAMPLE 1

Two electrodeionization devices, depicted in the exploded view of FIG. 1 and in the cross-sectional view of FIG. 2, were constructed. One electrodeionization device had a stack of 10 depleting compartments and concentrating compartments secured and held together by tie rods and nuts. The other electrodeionization device had a stack of 24 depleting and concentrating compartments. Depleting compartment spacer 18 and the concentrating compartment spacers 20 were molded using a rigid polymer available as RADEL® R-5100 polyphenylsulfone from BP Amoco Chemicals (Alpharetta, Ga.). A primary seal and a secondary seal were formed on opposite surfaces of the depleting compartment spacer. The primary seal included a groove and a resilient sealing member, in particular, an O-ring surrounding the cavity forming the depleting compartment. Upon assembly, resilient sealing members were compressed within the groove to form water-tight seals. The resilient sealing member was formed from an elastomeric material, having a lower hardness than the material forming the depleting compartment and concentrating compartment spacers. In particular, the resilient sealing members 26 were formed from silicone elastomer and buna-N elastomer.

EXAMPLE 2

An electrodeionization device having 10 depleting and concentrating compartment pairs was constructed as described above in Example 1 to evaluate its performance. The test system comprised a hot water source in a closed loop with the electrodeionization device. The electrodeionization device was cycled approximately three times per day with deionized water. The feed pressure into the electrodeionization device ranged from between 3–5 $psi_g$, with a dilute flow of 1 to 1.5 gallons per minute and a concentrate flow of 0.75 to 1.0 gallons per minute.

The typical sanitization cycle (HWS) comprised a one hour ramp up from 27° C. to 80° C., a one hour soak at 80° C. and a 20–30 minute cool down to 20° C. The electrodeionization device was allowed to sit at 27° C. for about 10 minutes before starting the next sanitization cycle.

After 7, 25, 52, 104 and 156 cycles, the electrodeionization device was checked for cross-leaks, and operated to evaluate changes in the rinse up curve. Rinse up shows how the quality of product increases as a function of time. After running for approximately 24 hours, the electrodeionization device was re-exposed to the sanitization cycles. The first three tests were performed with feed water temperature of below 10° C., while the later three tests were performed at 15° C. and 20° C.

Figure 3:
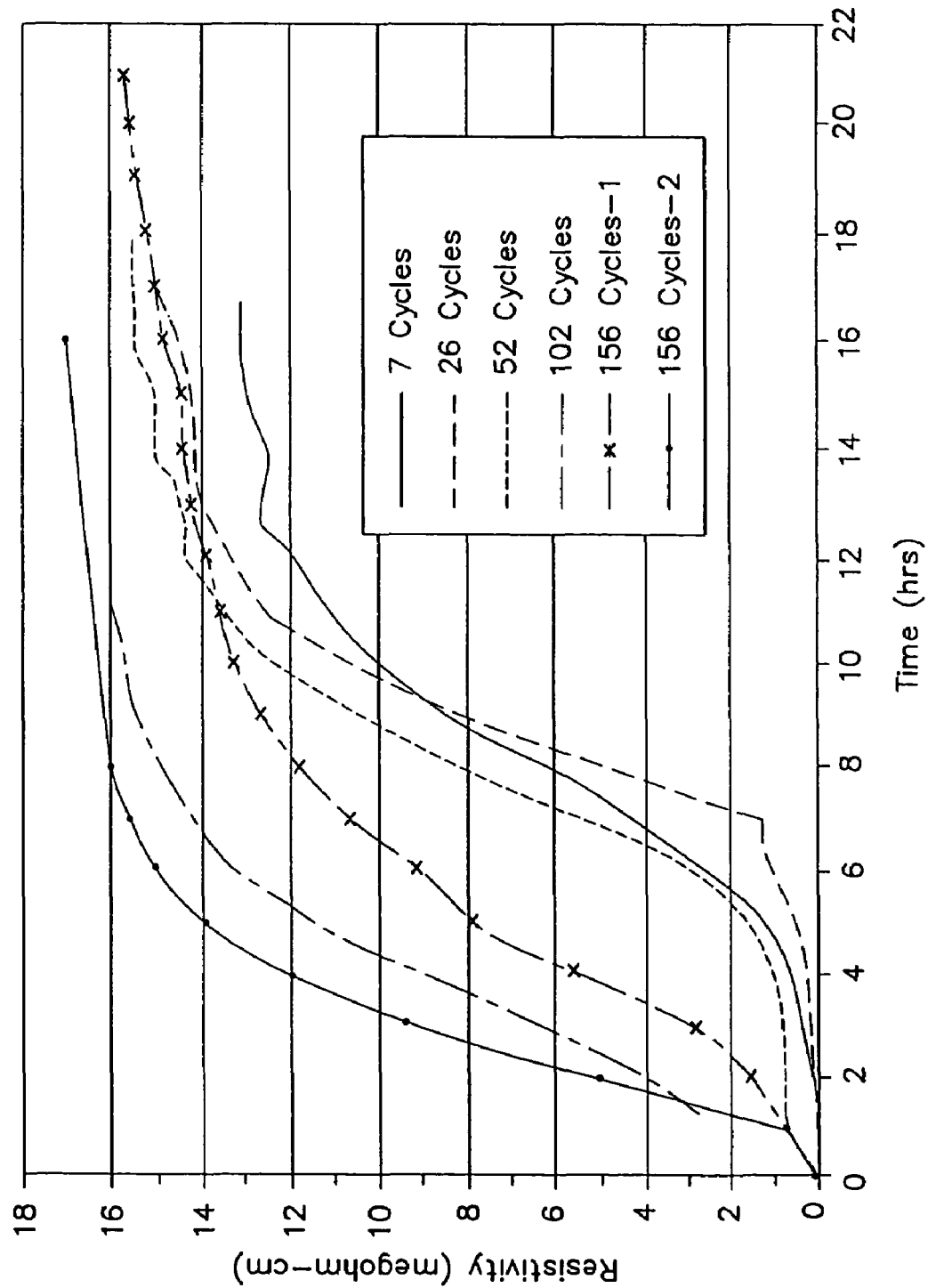
FIG. 3 is a graph showing rinse up curves after hot water cycling of the electrodeionization device of Example 2, showing the conductivity of purified water as a function of time.

FIG. 3 shows the resistivity, the quality of water, as a function of time after 7, 26, 52, 102 and 156 cycles. Notably, FIG. 3 showed that the resistivity, or the quality of the product water, improved with increasing number of hot water cycles. This figure also showed that the electrodeionization device can be used at higher temperatures, without component damage. In particular, this figure showed that the resin (which had been rated up to 60° C.) was suitable for sanitization cycles to 80° C., without a loss in electrodeionization device performance.

EXAMPLE 3

An electrodeionization device was constructed as described above in Example 1, and hot water, sanitized as described above in Example 2, was used to evaluate the effect of HWS on biological activity within the device. Initially, the electrodeionization device was placed on standby for about 6 days to increase the bacterial activity. Samples were taken before, during, and subsequent to sanitization at 80° C., and measured for colony forming units ("CFU"). Table 1 shows that during the hot water procedure, the concentration of colony forming units decreased.

TABLE 1

| Sample No | Sample | Mean (CFU/ml) |
|---|---|---|
| 1 | Feed. Power off. Recirculate 10 mins | >5000 |
| 2 | Product. Power off. Recirculate 10 mins | >5000 |
| 3 | Feed. Power off. Recirculate 30 mins | 1357 |
| 4 | Product. Power off. Recirculate 30 mins | 1188 |
| 5 | Feed. Power on, recirculate 30 mins | 1015 |
| 6 | Product. Power on, recirculate 30 mins | 221 |
| 7 | Feedwater/tank mid-sanitization cycle 80° C. | <0.1 |
| 8 | Feedwater/tank after sanitization cycle 72° C. | 1.3 |
| 9 | Feed after cool down w/RO permeate, Power on, single pass | 69 |
| 10 | Product after cool down w/RO permeate, Power on, single pass | 21 |

EXAMPLE 4

Two electrodeionization devices, a 10-cell and a 24-cell stack, were assembled as described above in Example 1. The electrodeionization devices were exposed to HWS at 80° C. as described in Example 2. Tables 2 and 3, listed below, summarize the operating conditions and performance of the devices and showed that the product quality, as measured by resistivity, increased after exposure to hot water cycling.

TABLE 2

| | 24-cell | |
|---|---|---|
| PARAMETER | Before HWS | After 2 HWS |
| Feed conductivity, μS/cm | 10.7 | 7.2 |
| Feed $CO_2$, ppm | 16–19 | 16–19 |
| Feed temperature, ° C. | 15–18.5 | 16–17 |
| DC volts | 193 | 205 |
| DC amps | 9.8 | 10.3 |
| Product flow, l/hr | 2000 | 2000 |
| Product resistivity, Megohm-cm | 7.1 | 15.2 |

TABLE 3

| | 10-cell | |
|---|---|---|
| PARAMETER | Before HWS | After 1 HWS |
| Feed conductivity, μS/cm | 1.2 | 1.1 |
| Feed $CO_2$, ppm | 2.5 | 2.5 |
| Feed temperature, ° C. | 15.2 | 16.1 |

TABLE 3-continued

| | 10-cell | |
|---|---|---|
| PARAMETER | Before HWS | After 1 HWS |
| DC volts | — | 40 |
| DC amps | 3 | 3 |
| Product flow, l/hr | 1000 | 1000 |
| Product resistivity, Megohm-cm | 15.8 | 18.1 |

EXAMPLE 5

In this example, a 10-cell pair LX electrodeionization module with Udel spacers and 3-layer resin configuration was aggressively hot water sanitized (HWS) at 85° C. and 30 $psi_g$ with rapid heating and cooling, for 156 cycles (the equivalent of 3 years of weekly sanitizations).

The LX modules were able to be hot water sanitized at 80° C. After 150 sanitization cycles at 80° C., there was no obvious external damage to the module. Module performance actually improved with successive sanitization cycles. Inlet pressure on the module was maintained at less than 10 $psi_g$, and the ramp-up cycle extended over an hour (1.6° C./min). Many of these operating limits were based on the operating parameters for hot water sanitizable RO (reverse osmosis) cartridges. It was also desired to shorten the sanitization cycle by heating the CDI modules up as rapidly as possible. This may also allow for simultaneous sanitization of downstream components (e.g., UV, filtration) and piping.

Udel polysulfone was used to make the spacers for the LX modules. All LX modules were initially constructed with a 4-layer resin configuration in the dilute compartments using Dow Monosphere 550A as the Type I anion resin. Subsequent testing showed that better silica removal and better performance on high $CO_2$ feeds was possible with a 3-layer configuration using Dow Marathon A as the Type I anion resin.

An LX pilot system constructed with CPVC piping was set up for automated hot water cycle testing. Automation included a Thornton 200CR with internal relays, a timing relay and four solenoid valves on the feed, product, concentrate, and cooling water lines. The heated water was supplied by a 30-gallon stainless steel tank with two immersion heaters, one in-line heater and a Grundfos CR-2 centrifugal pump, which were part of the adjacent continuous high temperature (CHT) RO system. An LX10module with 3 layer resin configuration was constructed by using cast aluminum end plates, machined polypropylene end blocks, and Udel dilute and concentrate spacers. The module was operated on RO water overnight prior to hot water sanitization to determine baseline performance. Operating conditions during rinseup were 5 gpm product flow and 0.5 gpm concentrate flow.

Hot water sanitization included pumping 85° C. deionized ("DI") water into the module at a flow of 2.5 gpm on the product side and 0.3 gpm on the concentrate side. Outlet diaphragm valves on the product and concentrate lines were adjusted to attain an inlet pressure of 30 $psi_g$ on both the dilute and concentrate. To maintain temperature, the hot product and concentrate streams were both returned to the feed tank. When the concentrate outlet temperature on the Thornton conductivity probe reached 85° C., the 60 minute recirculation of 85° C. water was initiated through the module. At the end of 60 minutes the hot DI water supply solenoid valve closed and the cool RO water solenoid valve opened. At this time, both the product and concentrate solenoid lines opened to drain. When the concentrate outlet temperature reached 25° C., the cool RO water solenoid valve closed, the hot DI water solenoid valve opened and both product and concentrate solenoid drain valves closed, initiating the next sanitization cycle.

After 26 sanitization cycles, the module was checked for tie rod torque and cross leaks. The module was then operated in service mode overnight on a blend of house RO & DI water (approximately 6 μS/cm feed). This was repeated every 26 sanitization cycles, after heat sanitation cycles 26, 52, 78, 104, 130, and 156. The number of cycles completed during each work day varied from 5 to 7, and the module was normally idle overnight (except for the periodic service mode mentioned above). The product water TOC (total organic carbon) was monitored on-line during several hot water sanitizations and rinseups. After 156 sanitation cycles, the module was checked for torque, for cross leaks, and allowed to rinse-up to quality for the better part of a week. The module was then autopsied.

Heating and cooling of the module was performed as quickly as the system would allow. The module feed water temperature changed from 25° C. to 85° C. within seconds, while the temperature on the concentrate outlet would usually take 3 to 4 minutes to reach set-point temperatures. In past CDI hot water cycle testing, the Thornton probes were located on the feed inlet and the product outlet. For this test, an additional probe was placed on the concentrate outlet stream. Since the concentrate flow was so much lower than the dilute flow (even during sanitization), this insured that the concentrate side of the module reached the 85° C. set point for the full 60-minute hold time.

The heating stand included two 8 kW immersion heaters and one 12 kW in-line heater, both controlled by separate mechanical temperature controllers. In practice the 85° C. set point varied by ±3° C. In addition to the set point variation, there also appeared to be some minor heat loss across the module. To attain 85° C. on the concentrate outlet required the feed inlet to be about 87° C. to 88° C.

After cool down, the solenoid drain valves close and the tank return valves opened. As hot water from the tank flowed into the module it forced the cold water that was presently in the module out and into the tank. If the tank temperature was at the low end of the set-point swing, it would sometimes took up to 15 minutes for the tank temperature to recover and raise the module temperature to 85° C.

Figure 4:
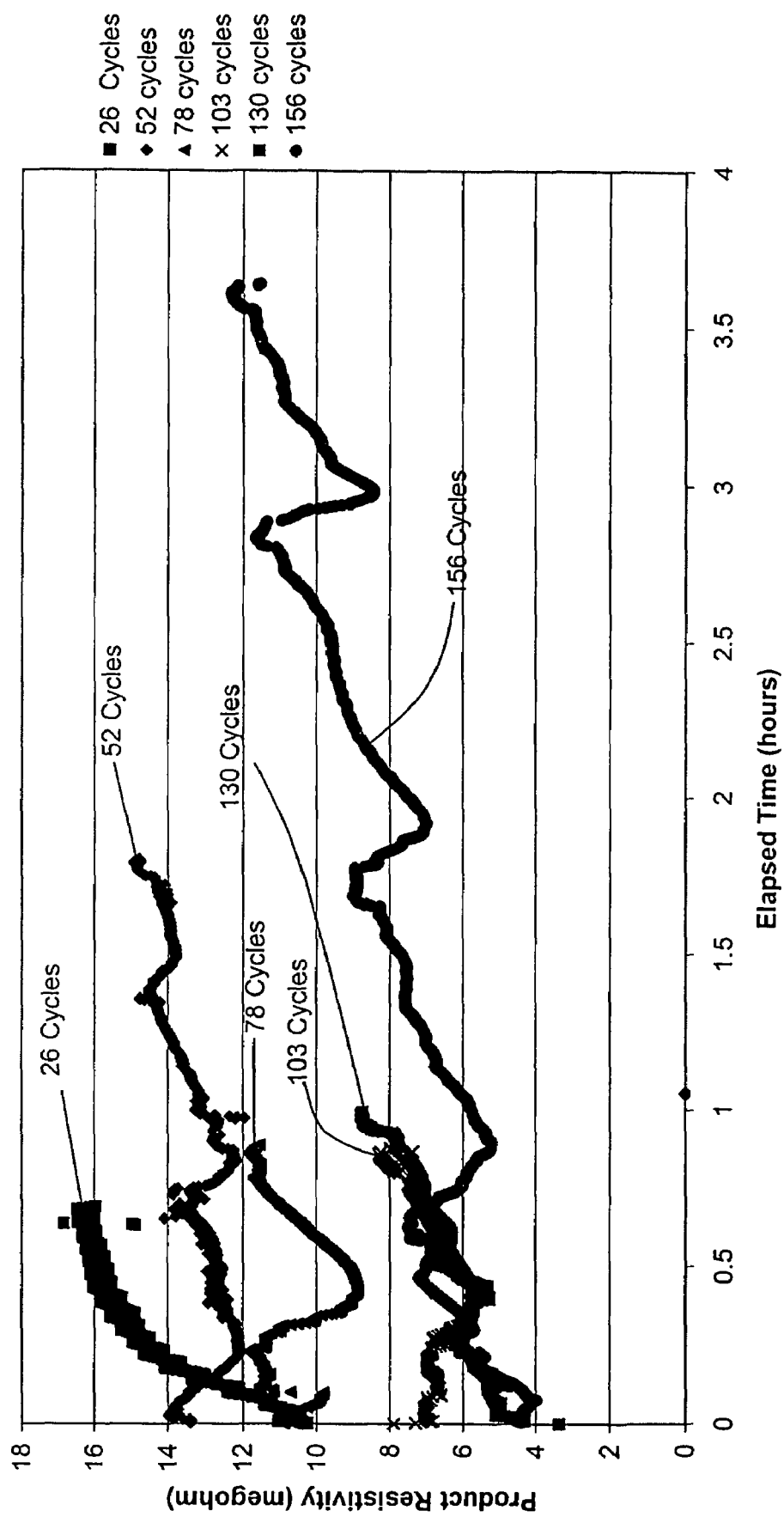
FIG. 4 is a graph showing product resistivity during rinse up of an electrodeionization device according to one embodiment of the invention.

Module performance during rinse-ups appeared to decline the more the module was sanitized, as illustrated in FIG. 4A. There was a concern that the slightly thicker Udel spacers may have led to resin slumping and thus the loss in performance. However, autopsy of the module revealed that resin slumping was not a problem; in fact the dilute and concentrate cells were slightly swelled.

Figure 5:
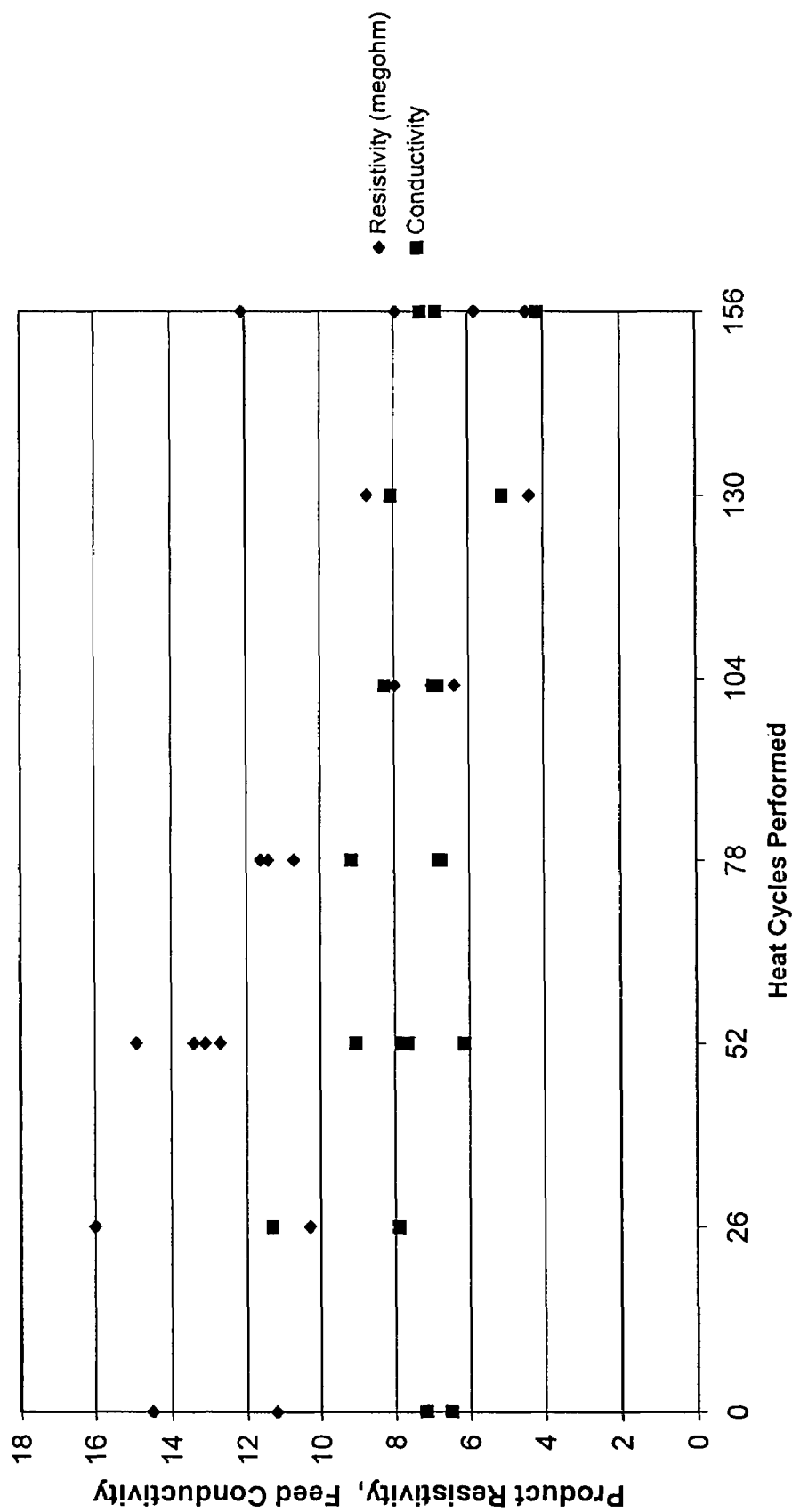
FIG. 5 is a graph showing resistivity and conductivity performance of an exemplary electrodeionization device of the invention.

FIG. 5 shows the feed conductivity and product resistivity at the beginning and end of each rinse-up after every 26 sanitation cycles. A blend of house RO and DI water was used to makeup the feed water to the CDI during rinse-up because the house RO conductivity was about 12–18 μS/cm. The water ranged between 4 and 12 μS/cm as the flow and RO quality changed throughout the day. Rinse-up of the module after sanitation was very slow. In most cases it was allowed to run overnight. CDI product quality during rinse-up seemed stable for the first 52 sanitation cycles. The feed temperature during rinse-up ranged from about 8° C. at the start of the experiment, to about 15° C. by the middle of the test, and was fairly stable from then on.

The pressure drop across the dilute side of the module was high from the start, but stable throughout the test at 36 psi$_d$. The low reading of 30 psi$_d$ at the start of the test was due to a low dilute flow of 4 gpm. The high reading at the end of the test of 48 psi$_d$ was due to the module being allowed to rinse-up for 5 days instead of overnight.

The module resistance at the beginning of each rinse-up ranged between 25 to 30 ohms. However after overnight rinse-up the module resistance was higher after each additional 26 sanitation cycles. Initially 29 ohms, the resistance later increased to over 50 ohms. Cross leak on the module was initially about 6 ml/5 minutes at 5 psi and ambient temperature. This increased to about 12 ml/5 minutes after completion of the 156 sanitations.

Figure 6:
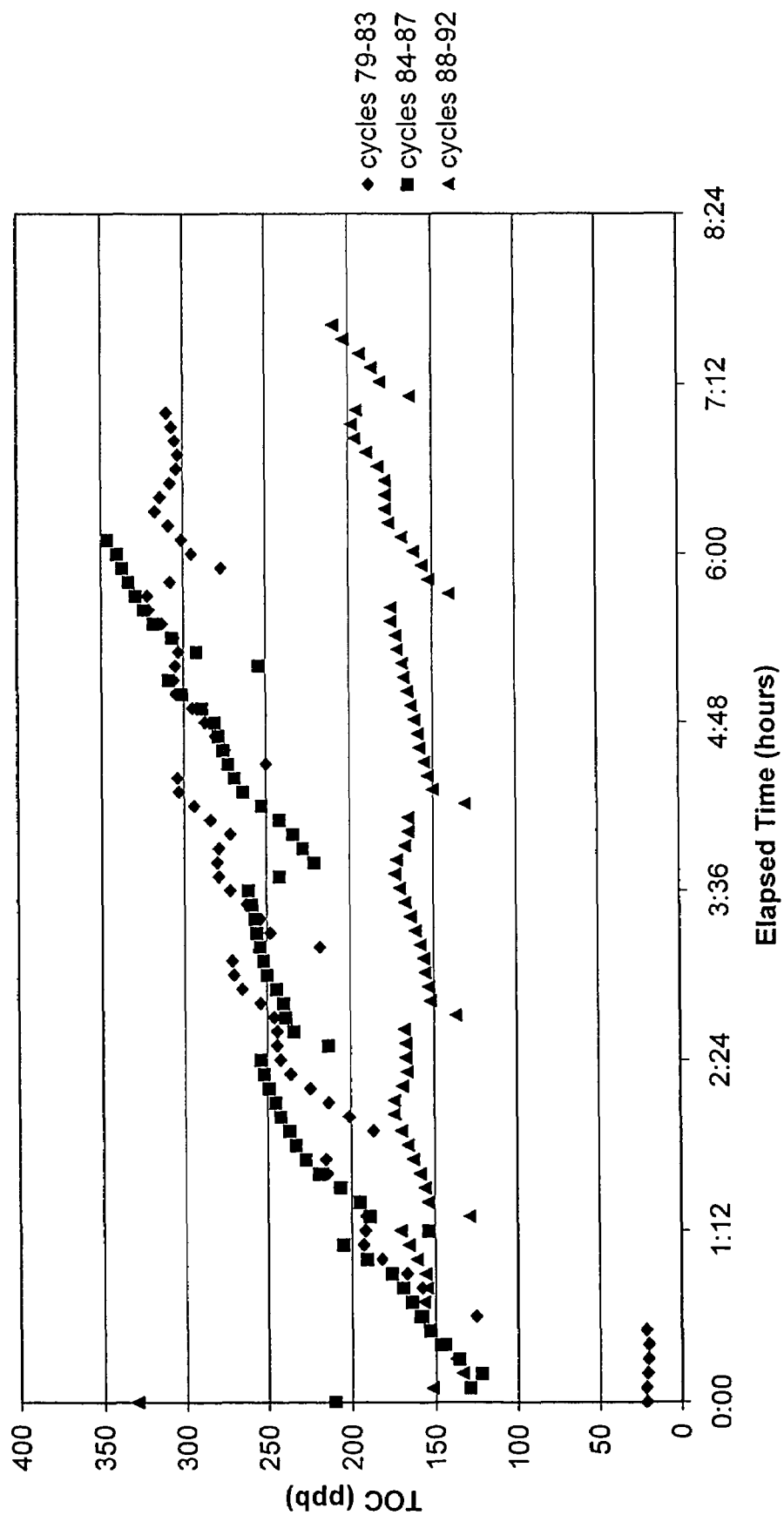
FIG. 6 is a graph of product water TOC levels during hot water sanitation of an electrodeionization device, in accordance with one embodiment of the invention.
Figure 7:
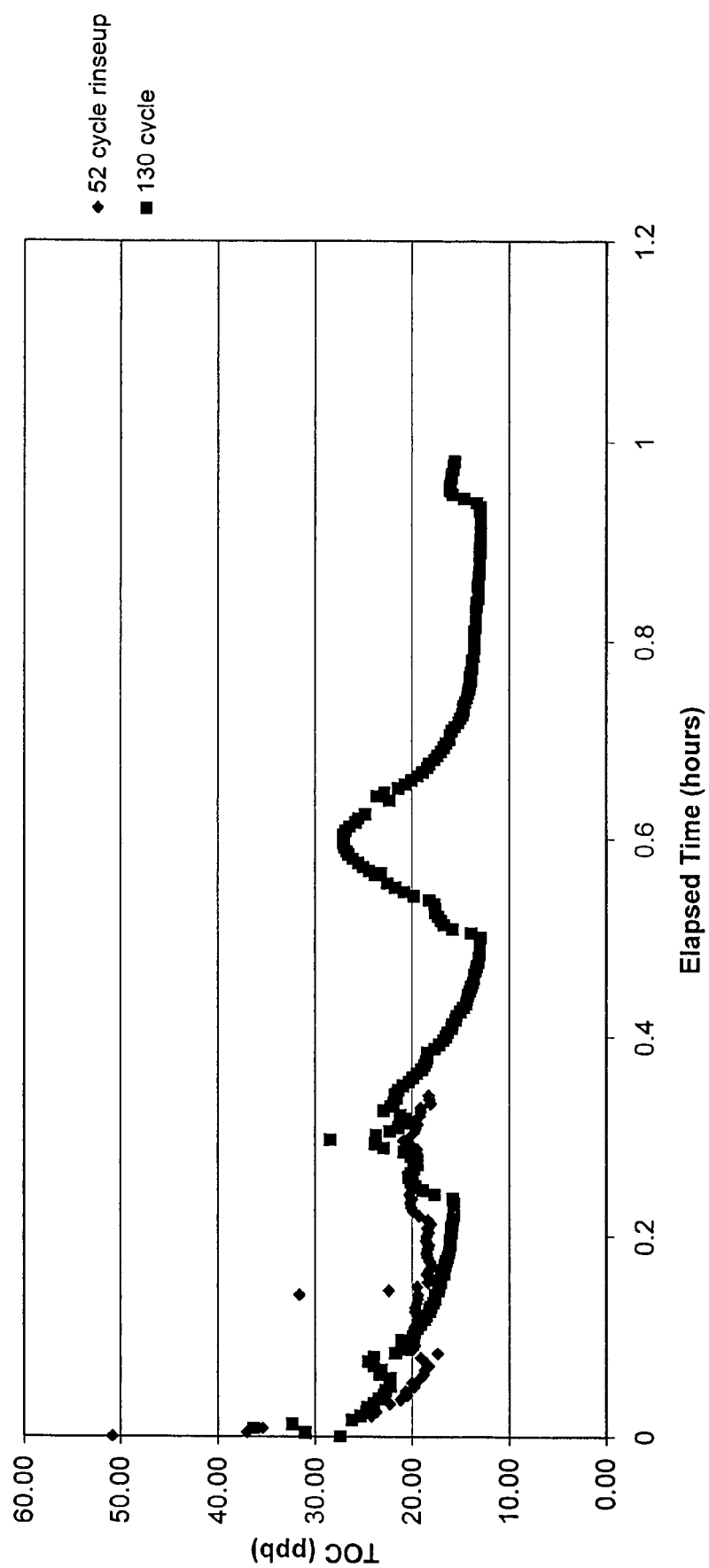
FIG. 7 is a graph of TOC levels during rinse up, according to another embodiment of the invention.

A Sievers 800 TOC analyzer was used on several occasions during this test to measure product water TOC on-line during hot water sanitation and during rinse-up after sanitation (FIGS. 6 and 7). TOC increased during hot water sanitations, and dropped slightly between sanitations, but generally increased with each additional sanitation. The TOC range during hot water sanitation was from 125 ppb to 350 ppb.

The module was shut down overnight. When sanitations resumed in the morning after the module had cooled, the TOC ranged from 125 to 150 ppb at startup. TOC was monitored during two of the rinse-ups, after sanitations 52 and 130. TOC at the start of rinse-up 52 was approximately 50 ppb, but quickly declined and stabilized at 20 ppb for the 8 hours it was operated. TOC during rinse-up 130 varied between 30 and 13 ppb for the 24 hours it was run. This variation in product TOC was probably due to variation in feed water.

In conclusion, heat sanitization at 85° C. and 30 psi$_g$ without temperature ramping did not appear to adversely affect the module mechanically, and TOC during and after hot water sanitation on a new module was well below the 500 ppb limit for pharmaceutical water applications.

Those skilled in the art would readily appreciate that all parameters and configurations described herein are meant to be exemplary and that actual parameters and configurations will depend on the specification application for which the systems and methods of the present invention are used. Those skilled in the art should recognize or be able to ascertain using no more than routine experimentation many equivalents to the specific embodiments of the invention described herein. For example, the present invention includes the use of a primary or a secondary water-tight seal that may be constructed or formed on either the depleting compartment or concentrating compartment spacers by any known technique such as molding or machining the grooves. It is, therefore, to be understood that the further embodiments are presented by way of example only and that, within the scope of the appended claims and equivalents thereto, the invention may be practiced otherwise as specifically described. The invention is directed to each individual feature, system, or method described herein. In addition, any combination of two or more such features, systems, or methods provided at such features, systems, or methods that are not mutually inconsistent, is included within the scope of the present invention.

The indefinite articles "a" and "an," as used herein in the specification and in the claims, unless clearly indicated to the contrary, should be understood to mean "at least one."

The phrase "and/or," as used herein, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified. Thus, as a non-limiting example, a reference to "A and/or B" can refer, in one embodiment, to A only (optionally including elements other than B); in another embodiment, to B only (optionally including elements other than A); in yet another embodiment, to both A and B (optionally including other elements); etc. As used herein, unless clearly indicated to the contrary, "or" should be understood to have the same meaning as "and/or." Only terms clearly indicated to the contrary, such as "only one of" or "exactly one of," will refer to the inclusion of exactly one element of a number or list of elements. In general, the term "or" as used herein shall only be interpreted as indicating exclusive alternatives (i.e. "one or the other but not both") when preceded by terms of exclusivity, such as "only one of" or "exactly one of."

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements that the phrase "at least one" refers to, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one act, the order of the acts of the method is not necessarily limited to the order in which the acts of the method are recited.

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A method of inactivating microorganisms in an electrodeionization device comprising:
   heating water to at least a pharmaceutically acceptable sanitization temperature externally of the electrodeionization device to produce a disinfecting solution;
   introducing the disinfecting solution into the electrodeionization device; and
   forcing the disinfecting solution at the at least pharmaceutically acceptable sanitization temperature from the electrodeionization device with water that is at about ambient temperature.

2. The method as in claim 1, wherein the step of introducing the disinfecting solution into the electrodeionization device comprises forcing liquid at about ambient temperature from the electrodeionization device with the disinfecting solution.

3. The method as claim 1, further comprising purifying water in the electrodeionization device to produce purified water.

4. The method as in claim 3, wherein the step of purifying the water in the electrodeionization device is performed with water that is at about ambient temperature.

5. The method as in claim 1, wherein the electrodeionization device comprises a depleting compartment spacer, a concentrating compartment spacer, a primary seal, and a secondary seal, wherein the primary and secondary seals are disposed between the depleting compartment and the concentrating compartment spacers.

6. The method as in claim 1, wherein the electrodeionization device comprises a spacer that is dimensionally stable at the at least pharmaceutically acceptable sanitization temperature.

7. The method as in claim 6, wherein the spacer comprises at least one of polysulfone, polyphenylsulfone, polyphenylene oxide, polyphenylene ether, and chlorinated poly (vinyl chloride).

8. The method as in claim 1, wherein the electrodeionization device comprises a depleting compartment spacer having a groove formed on a side thereon, a concentrating compartment spacer that mates with the depleting compartment spacer, and a resilient member disposed within the groove forming a water-tight seal between the depleting compartment and the concentrating compartment spacers.

9. The method as in claim 8, wherein the groove is disposed around a perimeter of the depleting compartment spacer.

10. The method as in claim 8, wherein the resilient member comprises at least one of a fluorinated elastomer and a silicone elastomer.

11. The method as in claim 1, wherein the disinfecting solution comprises at least one species selected from the group consisting of phenols, alcohols, halogens, heavy metals, quaternary ammonium compounds, detergents, and aldehydes.

12. The method of claim 1, further comprising maintaining the temperature of the disinfecting solution at the least pharmaceutically acceptable temperature for a predetermined period that reduces the number of active microorganisms in the electrodeionization device to a pharmaceutically acceptable level.

13. The method of claim 12, wherein the predetermined period is about sixty minutes.

14. The method of claim 1, further comprising circulating the disinfecting solution having the at least pharmaceutically acceptable sanitization temperature through the electrodeionization device.

15. The method of claim 14, wherein the step of circulating the disinfecting solution is performed for about sixty minutes.

16. The method of claim 14, wherein the step of circulating the disinfecting solution is performed until the number of active microorganisms within the electrodeionization device is reduced to a pharmaceutically acceptable level.

* * * * *